(12) United States Patent
Belloni et al.

(10) Patent No.: US 6,479,670 B1
(45) Date of Patent: Nov. 12, 2002

(54) SELECTIVE RETINOID ACID RECEPTOR AGONISTS

(75) Inventors: Paula Nanette Belloni, Half Moon Bay, CA (US); Peter Mohr, Basel (CH)

(73) Assignee: Hoffmann-La Roche Inc., Nutley, NJ (US)

( * ) Notice: Subject to any disclaimer, the term of this patent is extended or adjusted under 35 U.S.C. 154(b) by 231 days.

(21) Appl. No.: 09/614,331

(22) Filed: Jul. 12, 2000

(30) Foreign Application Priority Data

Aug. 25, 1999 (EP) .............................. 99116603

(51) Int. Cl.$^7$ ................. C07D 311/58; C07D 313/08; C07D 335/06; C07D 337/08
(52) U.S. Cl. .............. 549/9; 549/23; 549/355; 549/407
(58) Field of Search ............... 514/431, 432, 514/450, 456; 549/9, 23, 355, 407

(56) References Cited

FOREIGN PATENT DOCUMENTS

WO    WO 99/33821    7/1999

OTHER PUBLICATIONS

Massaro et al., Nature Medicine, 3, p. 675 (1997).
Massaro et al., Am. J. Physiol., 270, L305–L310 (1996).
H. Seager, Pharmaceutical Technology 9, (1985).

*Primary Examiner*—T. A. Sololu
(74) *Attorney, Agent, or Firm*—George W. Johnston; Dennis P. Tramaloni; F. Aaron Dubberley

(57) ABSTRACT

This invention relates to new selective retinoid acid receptor agonists of formula I

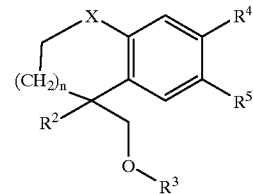

wherein the symbols are as defined in the specification to their pharmaceutically acceptable salts, individual isomers or to a racemic or non-racemic mixture; to pharmaceutical compositions containing them, and to methods for their use as therapeutic agents.

30 Claims, No Drawings

SELECTIVE RETINOID ACID RECEPTOR AGONISTS

FIELD OF THE INVENTION

This invention relates to new RAR selective retinoid agonists, to the use of such retinoic acid receptor agonists, particularly retinoic acid receptor γ selective agonists (RARγ-selective) for the treatment of emphysema.

BACKGROUND OF THE INVENTION

Chronic obstructive pulmonary disease (COPD) is a major cause of morbidity and mortality, ranking third and fourth as the leading cause of death in the European Union and North America respectively. COPD is characterized by reduced maximum expiratory flow, which does not change over several months and which persists for 2 or more consecutive years. Patients with the most severe form of COPD generally present with a significant degree of emphysema. Emphysema is defined anatomically by permanent airspace enlargement distal to the terminal bronchioles. It is characterized by gradual loss of lung recoil, alveolar destruction, decreased alveolar surface area and gas exchange, leading to a reduced FEV1. These two features, impaired gas exchange and reduction in expiratory flow, are characteristic physiological abnormalities from which patients with emphysema suffer. The main symptom of patients with severe emphysema is shortness of breath during minimal physical activity.

The most common cause of emphysema is cigarette smoking although other potential environmental toxins may also contribute. These various insulting agents activate destructive processes in the lung including release of active proteases and free radical oxidants in excess of protective mechanisms. The imbalance in protease/anti-protease levels leads to destruction of the elastin matrix, loss of elastic recoil, tissue damage and continuous decline in lung function. Removing the injurious agents (i.e. quit smoking) slows the rate of damage, however, the damaged alveolar structures do not repair and lung function is not regained.

Retinoic acid is a multifunctional modulator of cellular behavior, having the potential to alter both extracellular matrix metabolism and normal epithelial differentiation. In lung, retinoic acid has been shown to modulate various aspects of lung differentiation by interacting with specific retinoic acid receptors (RAR) that are selectively expressed temporally and spatially. Coordinated activation of RARβ and RARγ has been associated with lung branching and alveolization/septation. During alveolar septation, retinoic acid storage granules increase in the fibroblastic mesenchyme surrounding alveolar walls and RARγ expression in the lung peaks. Depletion of these retinyl-ester stores parallels the deposition of new elastin matrix and septation. In support of this concept, Massaro et al., Am. J. Physiol., 1996, 270, L305–L310, demonstrated that postnatal administration of retinoic acid increases the number of alveoli in rats. Furthermore, the capacity of dexamethasone to prevent the expression of CRBP and RARβ mRNA and subsequent alveolar septation in developing rat lung was abrogated by all-trans retinoic acid.

Recent studies demonstrated that all-trans retinoic acid can induce formation of new alveoli and return elastic recoil to near normal in animal models of emphysema, D. Massaro et el., Nature Medicine, 1997, 3, 675. However, the mechanism by which this occurs remains unclear.

Retinoids are a class of compounds structurally related to vitamin A, comprising natural and synthetic compounds.

Several series of retinoids have been found clinically useful in the treatment of dermatological and oncological diseases. Retinoic acid and its other naturally occurring retinoid analogs (9-cis retinoic acid, all-trans 3-4 didehydro retinoic acid, 4-oxo retinoic acid and retinol) are pleiotropic regulatory compounds that modulate the structure and function of a wide variety of inflammatory, immune and structural cells. They are important regulators of epithelial cell proliferation, differentiation and morphogenesis in lung. Retinoids exert their biological effects through a series of hormone nuclear receptors that are ligand inducible transcription factors belonging to the steroid/thyroid receptor superfamily. The retinoid receptors are classified into two families, the retinoic acid receptors (RARs) and the retinoid X receptors (RXRs), each consisting of three distinct subtypes (α, β, and γ). Each subtype of the RAR gene family encodes a variable number of isoforms arising from differential splicing of two primary RNA transcripts. All-trans retinoic acid is the physiological hormone for the retinoic acid receptors and binds with approximately equal affinity to all the three RAR subtypes, but does not bind to the RXR receptors for which 9-cis retinoic acid is the natural ligand.

In many non-pulmonary tissues, retinoids have anti-inflammatory effects, alter the progression of epithelial cell differentiation, and inhibit stromal cell matrix production. These properties have led to the development of topical and systemic retinoid therapeutics for dermatological disorders such as psoriasis, acne, and hypertrophic cutaneous scars. Other applications include the control of acute promyelocytic leukemia, adeno- and squamous cell carcinoma, and hepatic fibrosis. A limitation in the therapeutic use of retinoids outside of cancer has stemmed from the relative toxicity observed with the naturally occurring retinoids, all-trans retinoic acid and 9-cis retinoic acid. These natural ligands are non-selective and therefore have pleiotropic effects throughout the body, which are often toxic. Recently various retinoids have been described that interact selectively or specifically with the RAR or RXR receptors or with specific subtypes (α, β, γ) within a class.

SUMMARY OF THE INVENTION

This invention provides new RAR selective retinoid agonists of formula I

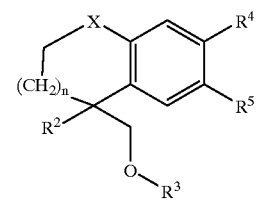

wherein
one of $R^4$ and $R^5$ is hydrogen and the other is

$R^1$ is hydrogen, lower alkyl;
$R^2$ is lower alkyl;
$R^3$ is lower alkyl or H;

X is oxygen or sulfur;

n is 1 or 2; and wherein the dotted bond is optional;

and pharmaceutically active salts of carboxylic acids of formula I.

The compounds of formula I contain a chiral carbon (to which $R^2$ is bound). These compounds may be present as a racemic mixture, i.e. (RS) or in the pure enantiomeric form as (S) or (R) isomer.

Activation of RAR has been associated with lung branching and alveolization. The retinoids according to the invention possess RAR agonist activity in vitro. Therefore such compounds would be useful for the treatment of emphysema and related pulmonary diseases. They may also be useful for the therapy and prophylaxis of dermatological disorders which are accompanied by epithelial lesions, e.g. acne and psoriasis, light- and age-damaged skin; as well as for the promotion of wound healing, for example of incised wounds, such as surgical wounds, wounds caused by burns and other wounds caused by cutaneous trauma; and for the therapy and prophylaxis of malignant and premalignant epithelial lesions, tumours and precancerous changes of the mucous membrane in the mouth, tongue, larynx, oesophagus, bladder, cervix and colon.

DETAILED DESCRIPTION OF THE INVENTION

When the dotted bond is present, a triple bond is meant, when the dotted bond is absent a double bond. Where the "dotted bond" is absent, the double bond may be "E" or "Z" configurated. The terms "E" and "Z" are used herein as defined in Pure and Applied Chem. 1976, 54, 12.

The term "lower alkyl" as used herein denotes straight chain or branched alkyl residues containing 1 to 5 carbon atoms, such as methyl, ethyl, propyl, isopropyl, butyl, isobutyl, tert.-butyl, pentyl, amyl and 3-pentyl.

The term "substantially free" of one or another isomer means that the ratio of the desired isomer to the undesired isomer is at least 95:5, more preferably at least 98:2. Resolution of the racemic mixture into either enantiomeric form can be performed in accordance with conventional techniques.

The compounds of formula I, wherein $R^1$ is hydrogen forms salts with pharmaceutically acceptable bases such as alkali salts, e.g. Na- and K-salts, and ammonium or substituted ammonium salts such as trimethylammonium salts which are within the scope of this invention.

Preferred compounds of formula I are the compounds of formula IA

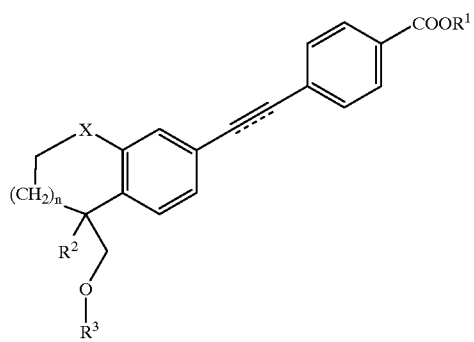

wherein X, $R^1$, $R^2$, $R^3$, n and the dotted bond are defined as above; and pharmaceutically active salts of carboxylic acids of formula IA.

Especially preferred compounds of formula IA are the compounds, wherein X is oxygen and n is 2, particularly compounds:

A  4-(5-methoxymethyl-5-methyl-2,3,4,5-tetrahydro-1-benzo[b]oxepin-8-yl-ethynyl)-benzoic acid B  4-(5-ethoxymethyl-5-methyl-2,3,4,5-tetrahydrobenzo[b]oxepin-8-ylethynyl)-benzoic acid C  4-(5-methyl-5-propoxymethyl-2,3,4,5-tetrahydrobenzo[b]oxepin-8-ylethynyl)-benzoic acid D  (E)-4-[2-(5-methoxymethyl-5-propyl-2,3,4,5-tetrahydrobenzo[b]oxepin-8-yl)-vinyl]-benzoic acid E  (E)-4-[2-(5-methoxymethyl-5-methyl-2,3,4,5-tetrahydrobenzo[b]oxepin-8-yl)-vinyl]-benzoic acid F  (E)-4-[2-(5-methyl-5-propoxymethyl-2,3,4,5-tetrahydrobenzo[b]oxepin-8-yl)-vinyl]-benzoic acid.

Further especially preferred are compounds of formula IA, wherein X is sulfur and n is 2, in particular the compounds:

G  4-(5-methoxymethyl-5-methyl-2,3,4,5-tetrahydrobenzo[b]thiepin-8-ylethynyl)-benzoic acid H  4-(5-ethoxymethyl-5-methyl-2,3,4,5-tetrahydrobenzo[b]thiepin-8-ylethynyl)-benzoic acid I  (E)-4-[2-(5-ethoxymethyl-5-methyl-2,3,4,5-tetrahydrobenzo[b]thiepin-8-yl)-vinyl]-benzoic acid J  (E)-4-[2-(5-methoxymethyl-5-propyl-2,3,4,5-tetrahydrobenzo[b]thiepin-8-yl)-vinyl]-benzoic acid.

A further preferred group of compounds are the compounds of formula IB

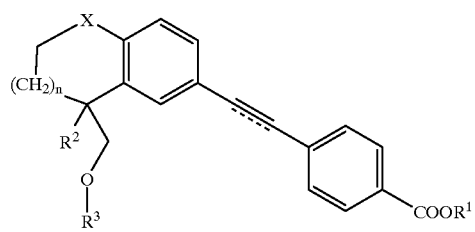

wherein X, $R^1$, $R^2$, $R^3$, n and the dotted bond are as defined above; and pharmaceutically active salts of carboxylic acids of formula IB.

Especially preferred compounds of formula IB are those wherein n is 1 and X is oxygen, for example the compounds:

K  4-(4-methoxymethyl-4-methyl-chroman-6-ylethynyl)-benzoic acid

L (E)-4-[2-(4-methoxymethyl-4-methyl-chroman-6-yl)-vinyl]-benzoic acid.

The compounds according to the invention can be prepared in a manner known in the art. Compounds of formula IA, wherein n is 1 or 2 and the dotted bond is present may be prepared according to the method depicted in scheme 1.

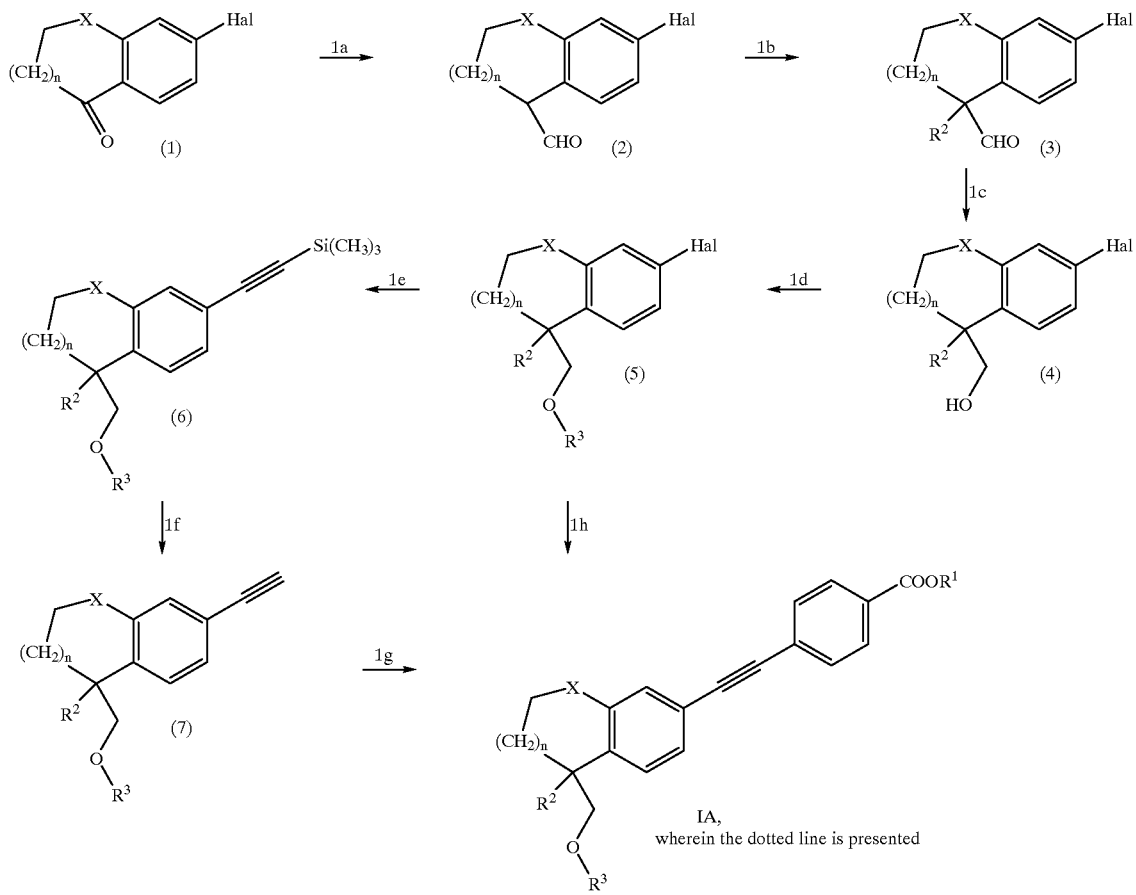

Scheme 1 wherein the symbols are as defined above and Hal is halogen such as iodine, bromine or chlorine.

Reaction Step 1a

A dihydrobenzo[b]oxepine- or dihydrobenzo[b]thiepine-one (1) is submitted to a Wittig-reaction with (methoxymethyl)triphenylphosphonium chloride in presence of a strong base, e.g. n-butyllithium, to form after acidic hydrolysis the aldehyde (2), the reaction is preferably carried out in a solvent as e.g. tetrahydrofuran (THF) at temperatures of about −78° to 0° C.

Reaction Step 1b

The carbaldehyde is then alkylated to (3) with an appropriate alkylhalogenide, preferably an alkyliodide in presence of a base as e.g. potassium tert.-butylate in a polar solvent, preferably in tert.-butanol. O-Alkylated side products can be separated and recycled if desired.

Reaction Step 1c

The reduction of the alkylated carbaldehyde (3) is preferably performed with sodium borohydride. The primary alcohol (4) obtained by this reduction is submitted to step 1d.

Reaction Step 1d

This etherification is preferably performed by deprotonation with a strong base as e.g. sodium hydride is a polar solvent, preferably N,N-dimethylformamide (DMF), and subsequent alkylation with an alkylhalogenide, preferably an alkyliodide.

Reaction Steps 1e, 1f and 1g

The halogenated tetrahydro-oxepine or -thiepine (5) is coupled with trimethylsilyl-acetylene in the presence of a base like piperidine or triethylamine and catalytic amounts of CuI, triphenylphosphine and bis(triphenylphoshpine) palladium (II) chloride or tetrakis-(triphenylphosphine)-palladium (0) to form the ethinylated derivative (6) (reaction step 1e).

After desilylation with catalytic amounts of sodium methylate in methanol to form compound (7) (reaction step 1f) alkyl-4-iodo-benzoate is attached by means of a second Sonogashira-coupling in the presence of a base like triethylamine and catalytic amounts of copper iodide, triphenylphosphine and bis(triphenylphosphine) palladium(II) chloride to yield the compound IA, wherein n is 2.

Reaction Step 1h

In the alternative shortcut, the halogenated tetrahydro-oxepine and -thiepine, respectively, (5) can be reacted directly with alkyl (4-ethynyl)benzoate as described in reaction step 1e in the presence of CuI, triphenylphosphine and tetrakis-(triphenylphosphine)-palladium (0) or bis-(triphenylphosphine)palladium (II) chloride to afford compound IA. However, if Hal is Br, the yields are satisfactory in the sulfur series only.

Compounds of formula IA, wherein the dotted bond is absent may be prepared according to the method depicted in scheme 2

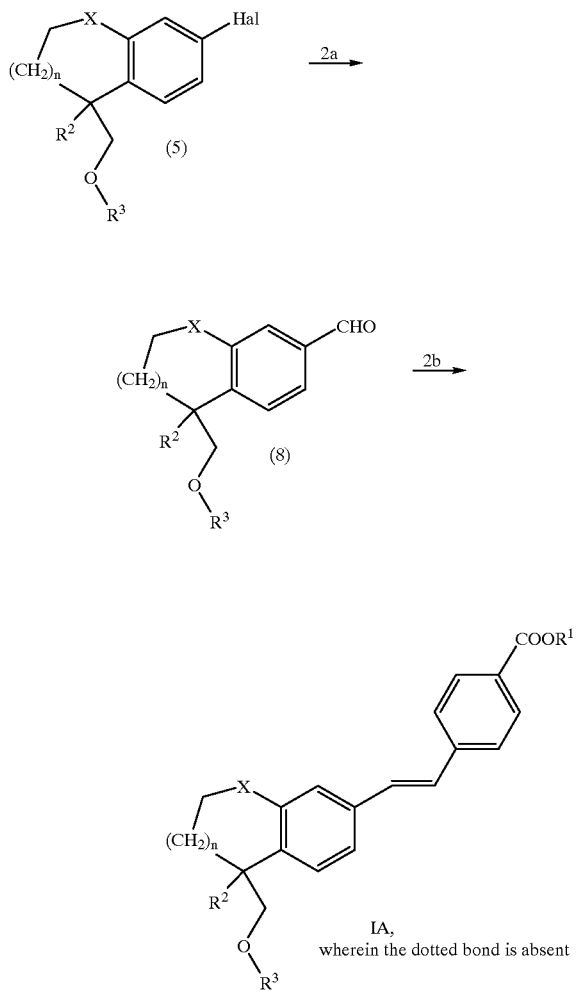

Scheme 2 wherein the symbols are as defined above.

Reaction Step 2a

The halogenated tetrahydro-oxepine or -thiepine, respectively, (5) is reacted subsequently with butyllithium and dimethyl formamide at −78° C. to yield after work-up with ammonium chloride the desired aldehyde (8).

Reaction Step 2b

The aldehyde (8) is then further elaborated via Wittig-Horner-reaction with the appropriate benzylic phosphonate in a polar aprotic solvent, preferably N,N-dimethylformamide or dimethylsulfoxide, in the presence of a strong base like sodium hydride, to afford trans-olefin IA. The Wittig-Horner reaction is highly "E" selective, and Schemes 2 and 4 illustrate synthesis of the "E" isomer. The corresponding "Z" isomer may be prepared in accordance with Scheme 1 or 3, followed by Lindlar reduction of the triple bond.

Compounds of formula IB, wherein n is 1 or 2 may be prepared according to the methods depicted in reaction schemes 3 and 4.

Scheme 3

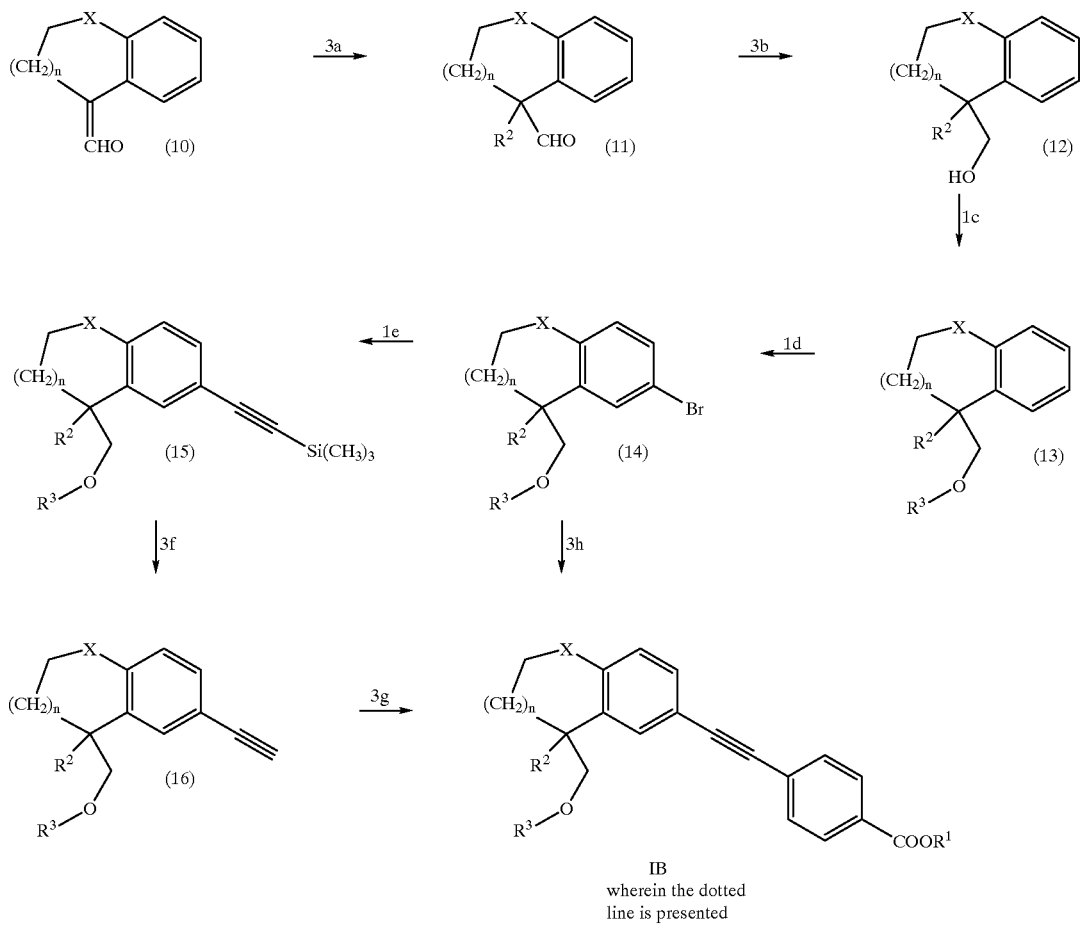

wherein the symbols are as defined above.

Scheme 4

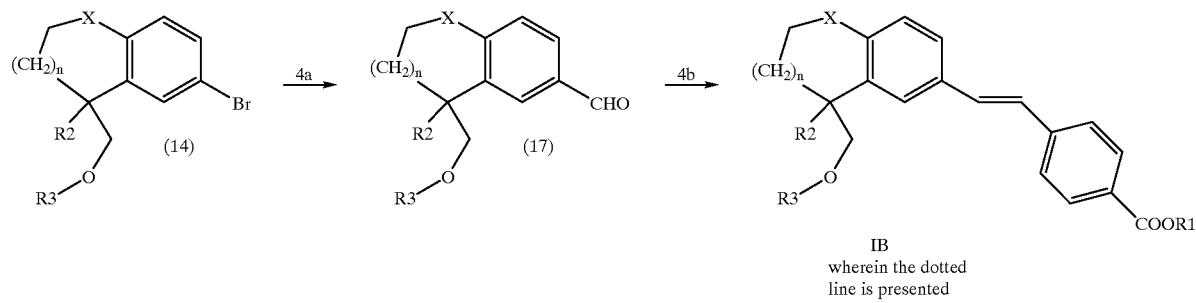

wherein the symbols are as defined above.

Whereas the compounds of formula IA can be prepared starting from meta-halogenated compounds (1), readily accessible from commercially available m-bromo-phenol and m-bromo-thiophenol, respectively; the compounds of formula IB are prepared starting from the not halogenated compounds (10), (prepared starting from phenol and thiophenol, respectively) which are functionalized at a later stage by conventional halogenation methods, see reaction step 3d. If $R^3$=H in compounds of formulae 1A and 1B, the primary hydroxy group must be suitably protected as e.g. acetate throughout the synthesis. Finally, the ester group $COOR^1$ of compounds of formula IA and IB can be hydrolyzed to the free acids according to standard conditions, e.g. with sodium hydroxide in THF/ethanol/acetone.

The starting compounds (1) and (10) can be made as illustrated in Scheme 5, or in analogy thereto.

Scheme 5

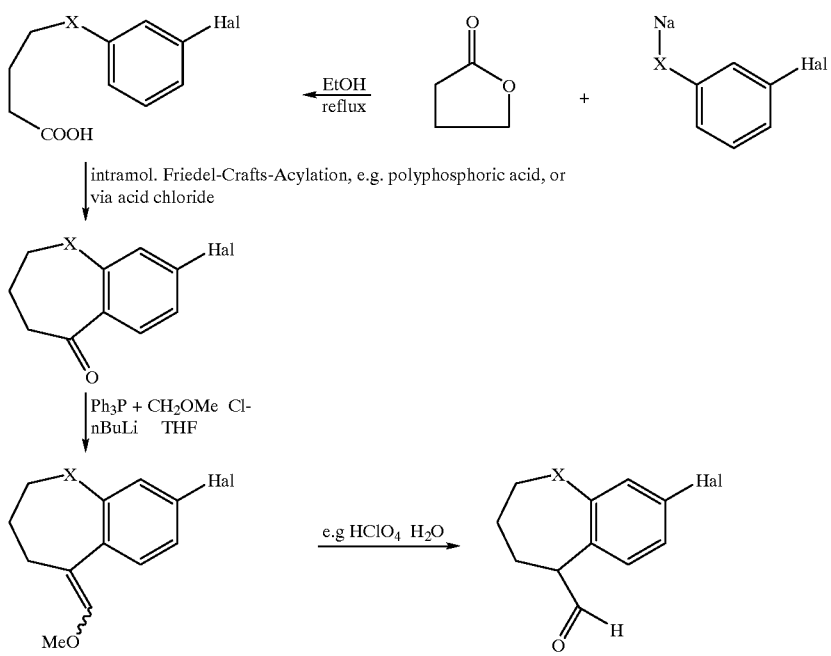

In another aspect, this invention is concerned with the use of RAR selective agonist with systemic administration being a preferred mode of delivery for treating emphysema and associated pulmonary diseases. It is thus concerned with a method for treating emphysema and associated pulmonary diseases by treatment of a mammal with a RAR selective agonist with systemic administration being a preferred mode of delivery.

A "therapeutically effective amount" means the amount of a compound that, when administered to a mammal for treating or preventing a disease, is sufficient to effect such treatment or prevention for the disease. The "therapeutically effective amount" will vary depending on the compound, the disease and its severity and the age, weight, etc., of the mammal to be treated.

The RARγ agonist selectivity of a compound can be determined by routine ligand binding assays known to one of skill in the art such as described in C. Apfel et al. *Proc. Nat. Sci. Acad. (USA)*, 89:7129–7133 (1992); M. Teng et al., *J. Med. Chem.*, 40:2445–2451 (1997); and PCT Publication WO 96/30009.

The use of RAR agonists disclosed herein may be used for promoting the repair of damaged alveoli and septation of new alveoli, particularly for the treatment emphysema. Treatment with RAR agonists, particularly RARγ selective agonists, is useful to promote repair of alveolar matrix and septation. As such, the methods disclosed herein are useful for treating diseases such as emphysema.

Typically, the dosage will range between about 0.01 and 1.0 mg/kg body weight per day, preferably from about 0.05 to about 0.5 mg/kg body weight per day.

In particular dosage of a RAR selective agonist required to treat lung emphysema will depend on the severity of the condition. This dosage may be delivered in a conventional pharmaceutical composition by a single administration, by multiple applications, or via controlled release, as needed to achieve the most effective results. Dosing will continue for as long as is medically indicated, which depending on the severity of the disease and may range from a few weeks to several months.

Typically, a pharmaceutically acceptable composition, such as a salt, of the RAR agonist of formula I in a pharmaceutically acceptable carrier or diluent is administered. In the context of the present invention, pharmaceutically acceptable salts include any chemically suitable salt known in the art of retinoid agonists as applicable for administration to human patients. Examples of conventional salts known in the art include the alkali metal salts such as sodium and potassium salts, the alkaline earth metal salts such as calcium and magnesium salts, and ammonium and alkyl ammonium salts.

Representative delivery regimens include oral, parenteral (including subcutaneous, intramuscular and intravenous), rectal, buccal (including sublingual), transdermal, pulmonary and intranasal. One method of pulmonary administration involves aerosolization of an aqueous solution of an RAR agonist. Aerosolized compositions may include the compound packaged in reverse micelles or liposomes. Typical pulmonary and respiratory delivery systems are described in U.S. Pat. Nos. 5,607,915, 5,238,683, 5,292,499, and 5,364,615.

The treatment methods of this invention also include systemic administration of RAR agonists in simultaneous or sequential combination with a further active ingredient.

RAR agonists will typically be administered as pharmaceutical compositions in admixture with a pharmaceutically acceptable, non toxic carrier. As mentioned above, such compositions may be prepared for parenteral (subcutaneous, intramuscular or intravenous) administration, particularly in the form of liquid solutions or suspensions; for oral or buccal administration, particularly in the form of tablets or capsules; for intranasal administration, particularly in the form of powders, nasal drops or aerosols; and for rectal or transdermal administration. Any conventional carrier material can be employed. The carrier material can be any organic or inorganic carrier material, such as water, gelatin, gum arabic, lactose, starch, magnesium stearate, talc, polyalkylene glycols, petroleum jelly and the like.

Liquid formulations for parenteral administration may contain as excipients sterile water or saline, alkylene glycols such as propylene glycol, polyalkylene glycols such as polyethylene glycol, oils of vegetable origin, hydrogenated naphthalenes and the like. They may employ slightly acidic buffers in pH ranges of about 4 to about 6. Suitable buffers include acetate, ascorbate and citrate at concentrations ranging from about 5 mM to about 50 mM. For oral administration, the formulation can be enhanced by the addition of bile salts or acylcarnitines.

Formulations for nasal administration may be solid and may contain excipients, for example, lactose or dextran, or may be aqueous or oily solutions for use in the form of nasal drops or metered spray. Particular nasal formulations include dry powders suitable for conventional dry powder inhalers (DPI's), liquid solutions or suspensions suitable for nebulization and propellant formulations suitable for use in metered dose inhalers (MDI's). For buccal administration typical excipients include sugars, calcium stearate, magnesium stearate, pregelatinated starch, and the like.

When formulated for nasal administration, the absorption across the nasal mucous membrane may be enhanced by surfactant acids, such as for example, glycocholic acid, cholic acid, taurocholic acid, ethocholic acid, deoxycholic acid, chenodeoxycholic acid, dehydrocholic acid, glycodeoxycholic acid, cyclodextrins and the like in an amount in the range between about 0.2 and 15 weight percent, preferably between about 0.5 and 4 weight percent, most preferably about 2 weight percent.

Solid forms for oral administration include tablets, hard and soft gelatin capsules, pills, sachets, powders, granules and the like. Each tablet, pill or sachet may contain from about 1 to about 50 mg, preferably from 5 to about 10 mg of RAR agonist of formula I. Preferred solid oral dosage forms include tablets, two-piece hard shell capsules and soft elastic gelatin (SEG) capsules. SEG capsules are of particular interest because they provide distinct advantages over the other two forms (see Seager, H., "Soft gelatin capsules: a solution to many tableting problems"; *Pharmaceutical Technology*, 9, (1985)). Some of the advantages of using SEG capsules are: a) dose-content uniformity is optimized in SEG capsules because the drug is dissolved or dispersed in a liquid that can be dosed into the capsules accurately b) drugs formulated as SEG capsules show good bioavailability because the drug is dissolved, solubilized or dispersed in an aqueous-miscible or oily liquid and therefore when released in the body the solutions dissolve or are emulsified to produce drug dispersions of high surface area and c) degradation of drugs that are sensitive to oxidation during long-term storage is prevented due to the dry shell.

Delivery of the compounds of the present invention to the subject over prolonged periods of time, for example, for periods of one week to one year, may be accomplished by a single administration of a controlled release system containing sufficient active ingredient for the desired release period. Various controlled release systems, such as monolithic or reservoir type microcapsules, depot implants, osmotic pumps, vesicles, micelles, liposomes, transdermal patches, iontophoretic devices and alternative injectable dosage forms may be utilized for this purpose. Localization at the site to which delivery of the active ingredient is desired is an additional feature of some controlled release devices, which may prove beneficial in the treatment of certain disorders.

The following are representative pharmaceutical formulations for using RAR selective agonists as described herein for promoting elastin mediated matrix repair and alveolar septation.

The following preparations and examples are given to enable those skilled in the art to more clearly understand and to practice the present invention. They should not be considered as limiting the scope of the invention, but merely as being illustrative and representative thereof.

Tablet Formulation

The following ingredients are mixed intimately and pressed into single scored tablets.

| Quantity per Ingredient | tablet, mg |
|---|---|
| RAR agonist of formula I | 10 |
| cornstarch | 50 |
| croscarmellose sodium | 25 |
| lactose | 120 |
| magnesium stearate | 5 |

Capsule Formulation

The following ingredients are mixed intimately and loaded into a hard-shell gelatin capsule.

| Ingredient | Quantity per capsule, mg |
|---|---|
| RAR agonist of formula I | 5 |
| lactose, spray-dried | 148 |
| magnesium stearate | 2 |

Suspension Formulation

The following ingredients are mixed to form a suspension for oral administration.

| Ingredient | Amount |
|---|---|
| RAR agonist of formula I | 1.0 g |
| fumaric acid | 0.5 g |
| sodium chloride | 2.0 g |
| methyl paraben | 0.15 g |
| propyl paraben | 0.05 g |
| granulated sugar | 25.5 g |
| sorbitol (70% solution) | 12.85 g |
| Veegum K (Vanderbilt Co.) | 1.0 g |
| flavoring | 0.035 ml |
| colorings | 0.5 mg |
| distilled water | q.s. to 100 ml |

Injectable Formulation

The following ingredients are mixed to form an injectable formulation.

| Ingredient | Amount |
|---|---|
| RAR agonist | 0.2 g |
| sodium acetate buffer solution, 0.4 M | 2.0 ml |
| HCl (1 N) or NaOH (1 N) | q.s. to suitable pH |
| water (distilled, sterile) | q.s. to 20 ml |

Nasal Formulation

The following ingredients are mixed to form a suspension for nasal administration.

| Ingredient | Amount |
| --- | --- |
| RAR agonist | 20 mg/ml |
| citric acid | 0.2 mg/ml |
| sodium citrate | 2.6 mg/ml |
| benzalkonium chloride | 0.2 mg/ml |
| sorbitol | 35 mg/ml |
| sodium taurocholate or glycocholate | 10 mg/ml |

The compounds prepared in the following examples have been prepared as racemic mixtures. However, the racemic mixtures can be easily resolved into the respective enantiomers according to well established methods, e.g. at the stage of the 2,3,4,5-tetrahydrobenzo[b]oxepinyl-methanol or 2,3,4,5-tetrahydrobenzo[b]thiepinyl-methanol, respectively. Such methods include separation by HPLC on a chiral column, e.g. a chiral NUCLEOSIL column; or separation by derivatization with a chiral acid, e.g. Mosher's acid, separation of the corresponding diastereomers by conventional techniques followed by reductive or hydrolytic cleavage of the ester.

EXAMPLE 1

1.1. Preparation of 4-(5-Methoxymethyl-5-methyl-2,3,4,5-tetrahydrobenzo[b]oxepin-8-ylethynyl)-benzoic acid

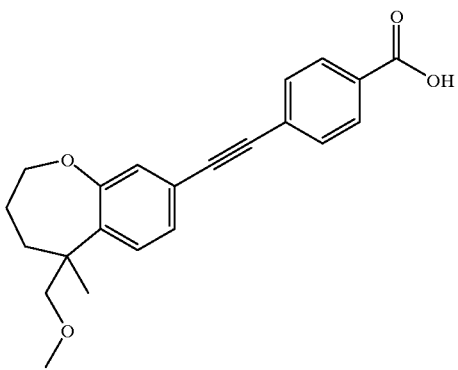

a] 8-Bromo-2,3,4,5-tetrahydrobenzo[b]oxepine-5-carbaldehyde 14.27 g (1.6 eq.) of (methoxymethyl)triphenylphosphonium chloride was suspended in 50 ml of abs. THF and deprotonated at a temperature of −10° C. and −5° C. by adding via syringe 25.2 ml of 1.6 M n-butyllithium (1.55 eq., in hexane). The resultant red ylide solution was cooled to −75° C. and treated with 6.20 g (26.0 mmol) of 8-bromo-3,4-dihydro-2H-benzo[b]oxepin-5-one dissolved in 13 ml of abs. THF. The mixture was then kept for 0.2 h at −78° C. and for 1 h at room temperature, poured onto crushed ice and extracted with diethylether. The organic phase was washed with water and dried over magnesium sulfate, filtrated and the solvent evaporated to yield a crude product which was purified by flash chromatography (SiO$_2$, hexane/ethylacetate=95/5). Thereby, 5.85 g of 8-bromo-5-methoxymethylene-2,3,4,5-tetrahydrobenzo[b]oxepine was obtained as E/Z-mixture which was hydrolyzed as follows:

This enolether (21.7 mmol) was dissolved in 30 ml of THF and then treated with 31.5 ml of 35% HClO$_4$. After stirring for 16 h, the resultant mixture was distributed between ice-cold water and diethylether. The organic layer washed with Na$_2$CO$_3$ (pH ca.10) and water, dried over magnesium sulfate, filtrated and the solvent evaporated to afford 4.63 g of the title compound as colorless oil (96% pure according to GC (gas chromatography)).

b] 8-Bromo-5-methyl-2,3,4,5-tetrahydrobenzo[b]oxepine-5-carbaldehyde 2.59 g (10.2 mmol) of 8-bromo-2,3,4,5-tetrahydrobenzo[b]oxepine-5-carbaldehyde was dissolved in 25 ml of abs. tert.-butanol. At 0° C. 2.28 g (2 eq.) of potassium tert.-butylate was added, followed by 1.58 ml (2.5 eq.) of methyliodide after 0.3 h. Stirring was continued at room temperature until TLC (thin layer chromatography) indicated the disappearance of starting material. The reaction mixture was then poured onto crushed ice and extracted twice with diethylether. The organic phase was washed with water, dried over magnesium sulfate, filtrated and the solvent evaporated under reduced pressure. Flash chromatography (SiO$_2$, hexane/ethylacetate 97/3) gave 1.85 g of the title compound as colorless oil (98% pure according to GC).

c] (8-Bromo-5-methyl-2,3,4,5-tetrahydrobenzo[b]oxepin-5-yl)-methanol 20.6 g (76.5 mmol) of 8-bromo-5-methyl-2,3,4,5-tetrahydrobenzo[b]oxepine-5-carbaldehyde was dissolved in 100 ml of abs. ethanol and cooled to 0° C. 2.896 g (1 mol-eq.) of NaBH$_4$ was added in several portions and the reaction allowed to proceed for 0.5 h at 0° C. and for 0.5 h at room temperature. The reaction mixture was poured onto crushed ice and extracted with diethylether. The organic phase was washed with water, dried over sodium sulfate and the solvent evaporated. Thereby were obtained 21.5 g of the title compound as colorless oil, sufficiently pure for the next step.

d] 8-Bromo-5-methoxymethyl-5-methyl-2,3,4,5-tetrahydrobenzo[b]oxepine

The above obtained primary alcohol (~76.5 mmol) was dissolved in 100 ml of abs. DMF and treated at −10° C. with 2.40 g of NaH (ca. 50% in mineral oil, ca. 1.3 eq.). Deprotonation was allowed to proceed at room temperature. When evolution of hydrogen had ceased, the mixture was cooled to 0° C., treated with 6.24 ml of methyliodide (1.3 eq.) and then kept for 0.2 h at 0° C. and for 0.75 h at room temperature (white precipitate of NaI formed). Hydrolysis with cold water, extraction with diethylether, washing the organic phase with NH$_4$Cl-solution, drying over sodium sulfate, filtration and evaporation of the solvent left a crude product, which was purified by filtration over SiO$_2$ (hexane/ethylacetate 95/5) to afford 22.5 g of the title product as colorless oil (96.5% pure according to GC).

e] (5-Methoxymethyl-5-methyl-2,3,4,5-tetrahydrobenzo[b]oxepin-8-ylethynyl)-trimethylsilane To 22.5 g (<76.5 mmol) of 8-bromo-5-methoxymethyl-5-methyl-2,3,4,5-tetrahydro-benzo[b]oxepine, dissolved in 50 ml of piperidine, was added successively 291 mg (0.02 eq.) of CuI, 401 mg (0.02 eq.) of triphenylphoshine (Ph$_3$P), and 884 mg (0.01 eq.) of (Ph$_3$P)$_4$Pd. After heating to 80° C., a solution of 26.5 ml (2.5 eq.) of trimethylsilylacetylene in 25 ml of piperidine was added within 1 h via dropping funnel. Since GC-analysis indicated, that 6% of starting material was still remaining, an additional amount of 3 ml of trimethylsilylacetylene was added in two portions. After cooling, the reaction mixture was poured onto crushed ice, extracted with diethylether, the organic phase washed with HCl dil., dried over sodium sulfate, filtrated and evaporated to dryness. Flash chromatography (SiO$_2$, hexane/ethylacetate 95/5) yielded 26.3 g of the title compound as yellowish oil, sufficiently pure for the next step (91% pure according to GC).

f] 8-Ethynyl-5-methoxymethyl-5-methyl-2,3,4,5-tetrahydrobenzo[b]oxepine

A small piece of sodium was dissolved in 100 ml of abs. methanol. The sodium methylate solution was added in one portion to 26.3 g (<76 mmol) of the above prepared 5-methoxy -methyl-5-methyl-2,3,4,5-tetrahydrobenzo[b]oxepin-8-ylethynyl)-trimethylsilane at 0° C. and then kept for 0.75 h at room temperature. The reaction mixture was poured on an aqueous saturated ammonium chloride solution and extracted with diethylether, the organic phase was separated, dried over sodium sulfate, filtrated and the solvents were removed. Flash chromatography (SiO$_2$, hexane/ethylacetate 96/4) yielded 15.60 g of the title compound as a pale yellow oil (96.5% pure according to GC).

g] 4-(5-Methoxymethyl-5-methyl-2,3,4,5-tetrahydrobenzo[b]oxepin-8-ylethynyl)-benzoic acid methyl ester In 165 ml of abs. DMF was successively dissolved 20.96 g (1.25 eq.) of methyl 4-iodo-benzoate, 2.29 g (0.04 eq.) of bis (triphenylphosphine)palladium(II) chloride, 1.86 g (0.12 eq.) of CuI, and 27.9 ml (2.5 eq.) of triethylamine. 14.67 g (63.7 mmol) of the above prepared 8-ethynyl-5-methoxymethyl-5-methyl-2,3,4,5-tetrahydrobenzo[b]oxepine, dissolved in 60 ml of abs. DMF, was added within 0.75 h via dropping funnel, 0.25 h later, the reaction was quenched by pouring the reaction mixture onto crushed ice/HCl, extracted with diethylether; the organic phase was washed with water, dried over sodium sulfate, filtrated and evaporated to dryness. Flash chromatography (SiO$_2$, hexane/ethylacetate 91/9) produced, after crystallization from the same solvent mixture, 19.5 g of the title compound as white crystals of m.p. 111.5–112.5° C.

h] 4-(5-Methoxymethyl-5-methyl-2,3,4,5-tetrahydrobenzo[b]oxepin-8-ylethynyl)-benzoic acid 20.06 g (55.04 mmol) of 4-(5-methoxymethyl-5-methyl-2,3,4,5-tetrahydrobenzo[b]oxepin-8-ylethynyl)-benzoic acid methyl ester was dissolved in 100 ml of THF/ethanol (1/1) and treated with 8.81 g (4 eq.) of NaOH, dissolved in 50 ml of water. The reaction flask was kept in the dark and stirring continued for 42 h at room temperature. The mixture was then poured onto crushed ice/60 ml of 25% HCl, extracted twice with ethylacetate; the organic phase was washed with a small amount of water, dried over sodium sulfate, filtrated, and evaporated to dryness. Crystallization from hexane/ethylacetate yielded 18.90 g of the title product as pale yellow crystals of m.p. 205–206° C.

Elemental Analysis: $C_{22}H_{22}O_4$ Calculated: C75.41% H6.33% Found: C75.31% H6.17%.

NMR: (1H, δ, TMS, CDCl$_3$) 1.40 (s, 3H), 1.59 (m, 1H), 1.9–2.15 (m, 3H), 3.36 (s, 3H), 3.37 (d, J=9, 1H), 3.83 (d, J=9, 1H), 3.85 (m, 1H), 4.10 (m, 1H), 7.18 (d, J=1, 1H), 7.23 (dxd, J=8, J=1, 1H), 7.28 (d, J=8, 1H), 7.60 (d, J=8.5, 2H), 8.09 (d, J=8.5, 2H).

1.2. Preparation of 4-(5-ethoxymethyl-5-methyl-2,3,4,5-tetrahydrobenzo[b]oxepin-8-ylethynyl)-benzoic acid

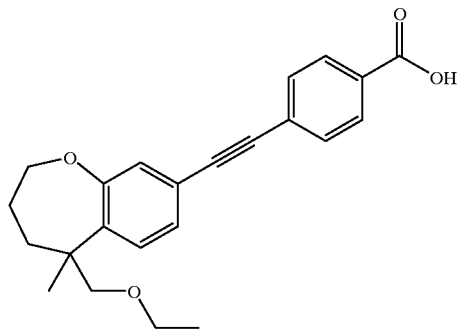

This compound was prepared in analogy to example 1.1. but using in step d] ethyliodide instead of methyliodide. White crystals of m.p. 170–171° C. were obtained. MS: (M)$^+$364, (M—CH$_2$OC$_2$H$_5$)$^+$305.

1.3. Preparation of 4-(5-methyl-5-propoxymethyl-2,3,4,5-tetrahydrobenzo[b]oxepin-8-ylethynyl)-benzoic acid

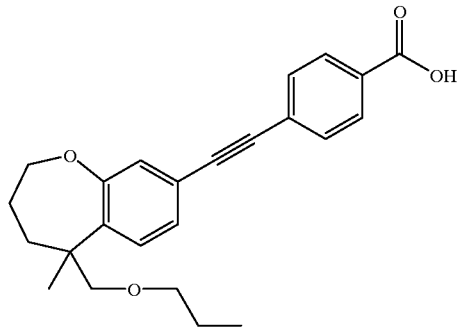

This compound was prepared in analogy to example 1.1. but using in step d] propyl iodide instead of methyl iodide. Off-white crystals of m.p. 148–149° C. were obtained. MS: (M)$^+$378, (M-CH$_2$OC$_3$H$_7$)$^+$305.

EXAMPLE 2

2.1. Preparation of 4-[2-(5-methoxymethyl-5-propyl-2,3,4,5-tetrahydrobenzo[b]oxepin-8-yl)-vinyl]-benzoic acid

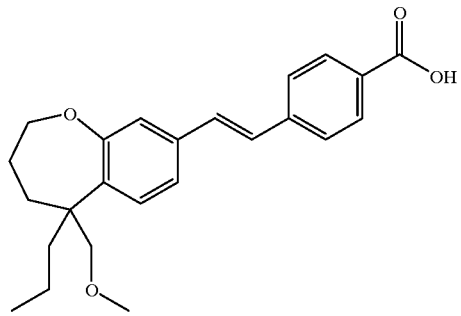

a] 5-Allyl-8-bromo-2,3,4,5-tetrahydrobenzo[b]oxepine-5-carbaldehyde 0.55 g (2.18 mmol) of 8-bromo-2,3,4,5-tetrahydrobenzo[b]oxepine-5-carbaldehyde (see example 1, step a]) was dissolved in 5 ml of abs. THF and 1 ml of abs. tert.-butanol. At 0° C. 0.490 g (2 eq.) of potassium tert.-butylate was added, followed by 0.552 ml (3 eq.) of allylbromide 0.1 h later. Stirring was continued at the same temperature until TLC (thin layer chromatography) indicated the disappearance of starting material. The reaction mixture was then poured onto crushed ice/$NH_4Cl$-solution, extracted twice with diethylether, the organic phase was washed with water, dried over sodium sulfate, filtrated and the solvents were removed. Flash chromatography (SiO2, hexane/ethylacetate 95/5) gave 0.224 g of the title compound as colorless oil (98% pure according to GC).

b] (5-Allyl-8-bromo-2,3,4,5-tetrahydrobenzo[b]oxepin-5-yl)-methanol 0.216 g (0.732 mmol) of 5-allyl-8-bromo-2,3,4,5-tetrahydrobenzo[b]oxepine-5-carbaldehyde was dissolved in 7 ml of abs. ethanol and cooled to 0° C. 0.028 g (1 mol-eq.) of $NaBH_4$ was added at once and the reaction allowed to proceed for 0.5 h at 0° C. Pouring onto crushed ice, twofold extraction with diethylether, washing the organic phase with water, and drying over sodium sulfate, filtrating and removing the solvent left 0.230 g of the title compound as colorless oil, sufficiently pure for the next step (96% pure according to GC).

c] (8-Bromo-5-propyl-2,3,4,5-tetrahydrobenzo[b]oxepin-5-yl)-methanol 0.230 g of the above prepared (5-allyl-8-bromo-2,3,4,5-tetrahydrobenzo[b]oxepin-5-yl) -methanol was dissolved in 10 ml of ethylacetate and hydrogenated over 0.20 g of 5% Pd/C during 0.5 h at room temperature and $1.01 \times 10^5$ Pa of $H_2$. The progress of the reaction must be followed carefully in order to avoid reductive removal of the bromine! After filtration over a pad of Celite the solvent was removed. Flash chromatography (SiO2, hexane/ethylacetate 8/2) produced 0.191 g of the title compound as colorless oil (GC-purity 91%).

In principle, this intermediate can also be prepared as described in example 1, step b] by using propyliodide for the alkylation. However, the yields are distinctively lower.

d] 8-Bromo-5-methoxymethyl-5-propyl-2,3,4,5-tetrahydrobenzo[b]oxepine 0.191 g (0.638 mmol) of (8-bromo-5-propyl-2,3,4,5-tetrahydrobenzo[b]oxepin-5-yl)-methanol was dissolved in 3 ml of abs. DMF and treated at 0° C. with 0.061 g of NaH (ca. 50% in mineral oil, ca. 2 eq.). Deprotonation was allowed to proceed at room temperature for 0.2 h. The mixture was cooled to 0° C., treated with 0.079 ml of methyliodide (2 eq.) and then kept for 1 h at room temperature. Hydrolysis with cold water, acidification with $NTH_4Cl$-solution, extraction with diethylether, drying the organic phase over sodium sulfate, filtration and evaporation of the solvents left a crude product, which was purified by flash chromatography (SiO2, hexane/ethylacetate 96/4) to give 0.179 g of the title compound as colorless oil (93% pure according to GC).

e] 5-Methoxymethyl-5-propyl -2,3,4,5-tetrahydrobenzo[b]oxepine-8-carbaldehyde 0.179 g (0.571 mmol) of 8-bromo-5-methoxymethyl-5-propyl-2,3,4,5-tetrahydrobenzo[b] oxepine was dissolved in 5 ml of abs. THF and cooled to −78°. 0.447 ml of n-butyllithium (1.5M, hexane) was slowly added and the temperature maintained for 0.2 h. 0.141 ml (3.2 eq.) of abs. DMF was introduced via syringe and stirring continued for 0.25 h. Warming to room temperature, pouring onto crushed ice/ $NH_4Cl$-solution, twofold extraction with diethylether, and drying the organic phase over sodium sulfate, filtration and evaporation of the solvent left 0.18 g of a crude product, which was purified by flash chromatography ($SiO_2$, hexane/ethylacetate 9/1) to give 0.125 g of the title compound as colorless oil (98% pure according to GC).

f] (E)-4-[2-(5-Methoxymethyl-5-propyl-2,3,4,5-tetrahydrobenzo[b]oxepin-8-yl)-vinyl]-benzoic acid ethyl ester 0.048 g of NaH (50% in mineral oil) was suspended in 3 ml of abs. DMF. 0.27 g of 4-(diethoxyphosphorylmethyl)-benzoic acid ethyl ester was added at 0° C. The mixture was stirred at room temperature, until $H_2$-formation had ceased. After cooling to −10° C., 0.119 g (0.454 mmol) of 5-methoxymethyl-5-propyl-2,3,4,5-tetrahydrobenzo[b]oxepine-8-carbaldehyde, dissolved in 2 ml of DMF, was added and allowed to react for 0.2 h at −10° C. and for 1 h at room temperature The mixture was then poured onto crushed ice/ $NH_4Cl$-solution, extracted with diethylether, the organic phase was washed with water, dried over sodium sulfate, filtrated and evaporated to dryness. Purification of the residue by flash chromatography (silica gel, hexane/ethylacetate 9/1) left finally 0.088 g of pure, colorless title compound which solidified spontaneously.

g] 4-[2-(5-Methoxymethyl-5-propyl-2,3,4,5-tetrahydrobenzo[b]oxepin-8-yl)-vinyl]-benzoic acid 0.081 g (0.198 mmol) of (E)-4-[2-(5-methoxymethyl-5-propyl-2,3,4,5-tetrahydrobenzo[b]oxepin-8-yl)-vinyl]-benzoic acid ethyl ester was dissolved in 1 ml of THF/ethanol (1/1) and treated with 0.33 ml of 3N NaOH (5 eq). The reaction flask was kept in the dark and stirring continued for 20 h at room temperature. The mixture was then poured onto crushed ice/diluted HCl, extracted twice with ethylacetate, the organic phase was washed with water, dried over sodium sulfate, filtrated and evaporated to dryness. Crystallization from hexane/ethylacetate yielded 0.46 g of the title product as white crystals of m.p. 157–159° C.

MS: $(M)^+380$, $(M-CH_2OCH_3)^+335$.

NMR: (1H, δ, TMS, DMSO)) 0.81 (t, J=7, 3H), 0.9–1.25 (m, 2H), 1.6–2.05 (m, 6H), 3.30 (s, 3H), 3.44 (d, J=9, 1H), 3.66 (d, J=9, 1H), 3.72 (m, 1H), 4.11 (m, 1H), 7.17 (d, J=8, 1H), 7.21 (d, J=1, 1H), 7.28 (dxt, J=8, J=1, 1H), 7.31 (br s, 2H), 7.70 (d, J=8, 2H), 7.93 (d, J=8, 2H), 12.91 (br s, COOH).

2.2. Preparation of (E)-4-[2-(5-methoxymethyl-5-methyl-2,3,4,5-tetrahydrobenzo[b]oxepin-8-yl)-vinyl]-benzoic acid

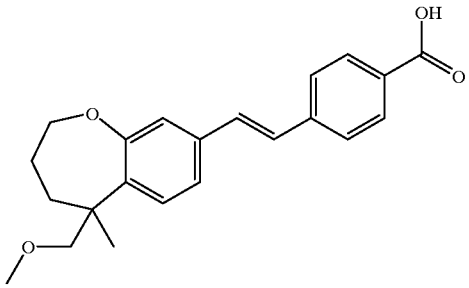

This compound was prepared in analogy to example 2.1., but using in step e] 8-bromo-5-methoxymethyl-5-methyl-2,3,4,5-tetrahydrobenzo[b]oxepine instead of the propyl-analogue. Colorless crystals of m.p. 194–96° C. were obtained.

CI–MS: $(M-H)^+351$.

IR($cm^{-1}$): 2667, 2546, 1688, 1606, 1567, 1419, 1291, 1238, 1179, 1080, 958, 871, 768.

NMR: (1H, δ, TMS, CDCl₃) 1.41 (s,3H), 1.59 (m, 1H), 1.9–2.15 (m, 3H), 3.37 (s,3H), 3.37 (d, J=9, 1H), 3.84 (d, J=9, 1H), 3.86 (m, 1H), 4.12 (m, 1H), 7.08–7.28 (m, 5H), 7.58 (d, J=8.2, 2H), 8.09 (d, J=8.2, 2H).

2.3. Preparation of (E)-4-[2-(5-methyl-5-propoxymethyl-2,3,4,5-tetrahydrobenzo[b]oxepin-8-yl)-vinyl]-benzoic acid

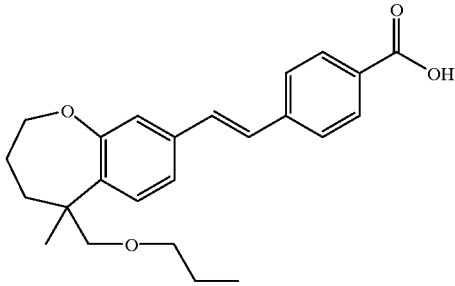

was prepared in analogy to example 2.1., but using in step e] 8-bromo-5-methyl-5-propoxymethyl-2,3,4,5-tetrahydrobenzo[b] oxepine instead of 8-bromo-5-methoxymethyl- 5-propyl-2,3,4,5-tetrahydrobenzo[b] oxepine. Colorless crystals of m.p. 164–65° C. were obtained.

MS: (M)⁺380, (M-CH₂OC₃H₇)⁺307.

2.4. Preparation of (E)-4-[2-(4-methoxymethyl-4-methyl-chroman-6-yl)-vinyl]-benzoic acid

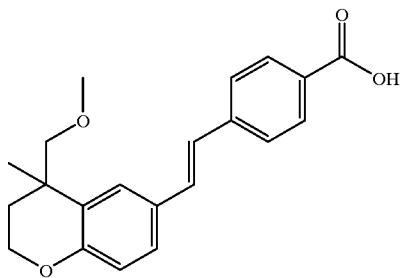

was prepared in analogy to Example 2.1., but using in step e] instead of 8-bromo-5-methoxymethyl-5-propyl-2,3,4,5-tetrahydrobenzo[b] oxepine 6-bromo-4-methoxymethyl-4-methyl-chroman, synthesis is described in Example 5 d]. Yellowish crystals of m.p. 209–210° C. were obtained.

NMR: (1H, δ, TMS, DMSO) 1.30 (s, 3H), 1.68 (dxdxd, 1H), 2.04 (dxdxd, 1H), 3.27 (s, 3H), 3.41 (d, J=9, 1H), 3.51 (d, J=9, 1H), 4.17 (m, 2H), ,6.77 (d, J=8, 1H), 7.18 (d, J=16, 1H) 7.32 (d, J=16, 1H), 7.38 (dxd, J=8, J=2, 1H), 7.60 (d, J=2, 1H), 7.66 (d, J=8.3, 2H) 7.91 (d, J=8.3, 2H).

CI-MS: (M–H)⁺337.

EXAMPLE 3

3.1. Preparation of 4-(5-methoxymethyl-5-methyl-2,3,4,5-tetrahydrobenzo[b]thiepin-8-ylethynyl)-benzoic acid

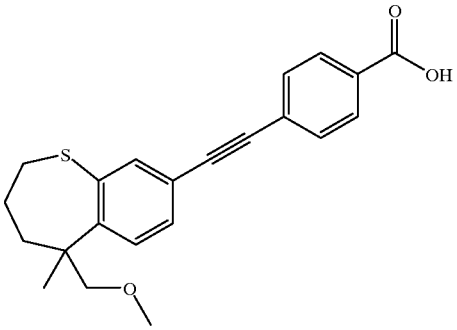

a] 8-Bromo-2,3,4,5-tetrahydrobenzo[b]thiepine-5-carbaldehyde 16.68 g (1.6 eq.) of (methoxymethyl) triphenylphosphonium chloride was suspended in 75 ml of abs. THF and deprotonated between –15° C. and –5° C. by adding via syringe 29.5 ml of 1.6 M n-butyllithium (hexane, 1.55 eq.). The resultant red ylide solution was cooled to –75° C. and treated with 7.82 g (30.4 mmol) of 8-bromo-3,4-dihydro-2H-benzo[b]thiepin-5-one, dissolved in 15 ml of abs. THF. The mixture was then kept for 0.3 h at –78° C. and for 1.25 h at room temperature. Pouring onto crushed ice, twofold extraction with diethylether, washing the organic phase with water, drying over magnesium sulfate, filtration and evaporation of the solvents yielded a crude product which was purified by flash chromatography (SiO₂, hexane/ethylacetate 95/5); thereby, 7.39 g of 8-bromo-5-methoxymethylene-2,3,4,5-tetrahydrobenzo[b]thiepine was obtained as E/Z-mixture which was hydrolyzed as follows:

This enolether (25.8 mmol) was dissolved in 37 ml of THF and then treated with 37 ml of 35% HClO₄. After stirring for 16 h at room temperature, the resultant mixture was distributed between ice-cold water and diethylether, the organic layer was washed twice with Na₂CO₃ (pH ca.10) and water, dried over magnesium sulfate, filtrated and evaporated to dryness. Purification of the residue by flash chromatography (silica gel, hexane/ethylacetate 95/5) left finally 6.33 g of the title compound as colorless oil (98% pure according to GC).

MS: (M)⁺270,272, (M-CO)⁺242,244.

b] 8-Bromo-5-methyl-2,3,4,5-tetrahydrobenzo[b]thiepine-5-carbaldehyde 1.00 g (3.69 mmol) of 8-bromo-2,3,4,5-tetrahydrobenzo [b]thiepine-5-carbaldehyde was dissolved in 8 ml of abs. THF/abs. tert.-butanol (10/1). At 0° C. 0.828 g (2 eq.) of potassium tert.-butylate was added, followed by 0.575 ml (2.5 eq.) of methyliodide after 0.25 h. Stirring was continued for 5 h at room temperature. The reaction mixture was then poured onto crushed ice and extracted twice with diethylether, the organic phase was washed with brine, dried over magnesium sulfate, filtrated and the solvent was removed. Flash chromatography (SiO2, hexane/ethylacetate 96/4) gave 0.636 g of the title compound as colorless oil.

c] (8-Bromo-5-methyl-2,3,4,5-tetrahydrobenzo[b]thiepin-5-yl)-methanol 636 mg (2.23 mmol) of 8-bromo-5-methyl-2,3,4,5-tetrahydrobenzo[b]thiepine-5-carbaldehyde was dissolved in 15 ml of abs. ethanol and cooled to 0° C. 84.4 mg (1 mol-eq.) of NaBH$_4$ was added and the reaction allowed to proceed for 2 h at room temperature. Pouring onto crushed ice, extraction with diethylether, washing the organic phase with water, drying over magnesium sulfate, filtration and evaporation of the solvent left 628 mg of the title compound as white solid, which was used in the next step without further purification (93.5% pure according to GC).

d] 8-Bromo-5-methoxymethyl-5-methyl-2,3,4,5-tetrahydrobenzo[b]thiepine 628 mg (2.19 mmol) of (8-bromo-5-methyl-2,3,4,5-tetrahydrobenzo[b]thiepin-5-yl)-methanol was dissolved in 12 ml of abs. DMF and treated at 0° C. with 210 mg of NaH (ca. 50% in mineral oil, ca. 2 eq.). Deprotonation was allowed to proceed at 0° C. for 1 h. The resultant solution of the corresponding sodium alkoxide was then treated with 0.204 ml of methyliodide (1.5 eq.) and kept for 2 h at room temperature. Hydrolysis with cold water, extraction with diethylether, washing the organic phase with water, drying it over magnesium sulfate, filtration and evaporation of the solvent left a crude product, which was purified by filtration over SiO$_2$ (hexane/ethylacetate 96/4) to produce 576 mg of the title compound as colorless oil (95% pure according to GC).

MS: (M)$^+$300,302, (M-CH$_2$OCH$_3$)$^+$255,257.

e] 4-(5-Methoxymethyl-5-methyl-2,3,4,5-tetrahydrobenzo[b]thiepin-8-ylethynyl)-benzoic acid methyl ester To 478 mg (1.59 mmol) of 8-bromo-5-methoxymethyl-5-methyl-2,3,4,5-tetrahydrobenzo[b]thiepine, dissolved in 2.9 ml of piperidine, was added successively 4.8 mg (0.02 eq.) of CuI, 7.0 mg (0.02 eq.) of Ph$_3$P, and 24.1 mg (0.01 eq.) of (Ph$_3$P)$_4$Pd. After heating to 80° C., a solution of 508 mg (2 eq.) of 4-ethynyl-benzoic acid methyl ester in 2.8 ml of piperidine was added within 2 h via dropping funnel and then kept at this temperature for 3 additional h. After cooling, the reaction mixture was poured onto crushed ice/ HCl diluted, extracted with diethylether, the organic phase was washed with water, dried over magnesium sulfate, filtrated and evaporated to dryness. Flash chromatography (SiO$_2$, hexane/ethylacetate 95/5) yielded 270 mg of the title compound as colorless oil.

MS: (M)$^+$380, (M-CH$_2$OCH$_3$) 335.

f] 4-(5-Methoxymethyl-5-methyl-2,3,4,5-tetrahydrobenzo[b]thiepin-8-ylethynyl)-benzoic acid 316 mg (0.83 mmol) of 4-(5-methoxymethyl-5-methyl-2,3,4,5-tetrahydrobenzo[b]thiepin-8-ylethynyl)-benzoic acid methyl ester was dissolved in 8 ml of THF/EtOH (1/1) and treated with 1.38 ml of 3N NaOH (5 eq.). The reaction flask was kept in the dark and stirring continued for 18 h at room temperature. The mixture was then poured onto crushed ice/ HCl, extracted twice with diethylether, the organic phase was washed with brine, dried over magnesium sulfate, filtrated and evaporated to dryness. Crystallization of the residue from hexane/ethylacetate yielded 282 mg of the title product as white crystals of m.p. 182–183° C.

NMR: (1H, δ, TMS, CDCl$_3$) 1.51 (s, 3H), 1.74 (m, 1H), 1.99 (m, 1H), 2.13 (m, 2H), 2.77 (t, J=6, 2H), 3.37 (s, 3H), 3.65 (d, J=9, 1H), 3.95 (d, J=9, 1H), 7.38 (s, 2H), 7.60 (d, J=8.4, 2H), 7.72 (s, 1H), 8.09 (d, J=8.4, 2H).

MS: (M)$^+$366, (M-CH$_2$OCH$_3$)$^+$321.

3.2. Preparation of 4-(5-ethoxymethyl-5-methyl-2,3,4,5-tetrahydrobenzo[b]thiepin-8-ylethynyl)-benzoic acid

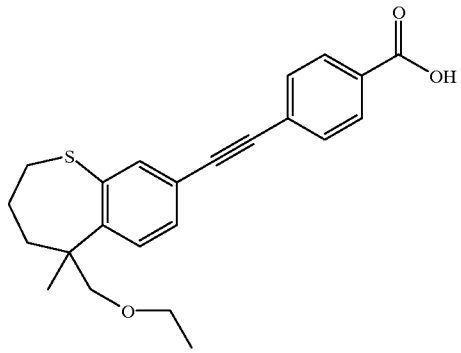

This compound was prepared in analogy to Example 3.1., but using in step e] 8-bromo-5-ethoxymethyl-5-methyl-2,3,4,5-tetrahydrobenzo[b]thiepine instead of the 5-methoxymethyl -derivative. White crystals of m.p. 154–155° C. were obtained.

MS: (M)$^+$380, (M-CH$_2$OC$_2$H$_5$)$^+$321.

EXAMPLE 4

4.1. Preparation of (E)-4-[2-(5-ethoxymethyl-5-methyl-2,3,4,5-tetrahydrobenzo[b]thiepin-8-yl)-vinyl]-benzoic acid

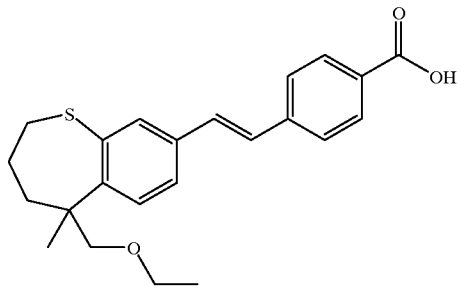

a] 8-Bromo-5-ethoxymethyl-5-methyl-2,3,4,5-tetrahydrobenzo[b]thiepine 917 mg (3.19 mmol) of (8-bromo-5-methyl-2,3,4,5-tetrahydrobenzo[b]thiepin-5-yl)-methanol (Example 3.1. c]) was dissolved in 17 ml of abs. DMF and treated at 0° C. with 309 mg of NaH (ca. 50% in mineral oil, ca. 2 eq.). Deprotonation was allowed to proceed at 0° C. for 0.25 h. The resultant solution of the corresponding sodium alkoxide was then treated with 0.389 ml of ethyliodide (1.5 eq.) and kept for 1 h at room temperature. Hydrolysis with cold water, extraction with diethylether, washing the organic phase with water, drying it over magnesium sulfate, filtration and evaporation of the solvent left a crude product, which was purified by filtration over SiO$_2$ (hexane/ethylacetate 95/5) to produce 966 mg of the title compound as colorless oil (98% pure according to GC).

b] 5-Ethoxymethyl-5-methyl-2,3,4,5-tetrahydrobenzo[b]thiepine-8-carbaldehyde 431 mg (1.37 mmol) of 8-bromo-5-ethoxymethyl-5-methyl-2,3,4,3-tetrahydrobenzo[b]thiepine was dissolved in 3.5 ml of abs. THF and cooled to −78° C. 0.97 ml of n-butyllithium (1.55M, hexane) was slowly added and the temperature maintained for 0.3 h. 0.316 ml (3eq.) of abs.

DMF was introduced via syringe and stirring continued for 0.1 h at −78° C. Warming the reaction mixture to room temperature, pouring it onto crushed ice, and extract it with diethylether, washing the organic phase with water, and drying it over sodium sulfate left after filtration and evaporation of the solvent a crude product, which was purified by flash chromatography (SiO$_2$, hexane/ethylacetate 95/5) to give 0.339 g of the title compound as colorless oil (99% pure according to GC).

c] (E)-4-]2-(5-Ethoxymethyl-5-methyl-2,3,4,5-tetrahydrobenzo[b]thiepin-8-yl)-vinyl]benzoic acid methyl ester 85 mg of NaH (ca. 1.4 eq., 50% in mineral oil) was added to a solution of 534 mg (1.4 eq.) of 4-(diethoxyphosphorylmethyl)-benzoic acid ethyl ester in 1.9 ml of abs. DMF at 0° C. The mixture was stirred at 0° C. for 0.5 h and at room temperature for 1.5 h. After cooling to 0° C., 336 mg (1.27 mmol) of 5-ethoxymethyl-5-methyl-2,3,4,5-tetrahydrobenzo[b]thiepine-8-carbaldehyde, dissolved in 1 ml of DMF, was added and allowed to react for 2 h at room temperature. The mixture was then poured onto crushed ice, extracted twice with diethylether, the organic phase was washed with water, dried over magnesium sulfate, filtrated and evaporated to dryness. Purification of the residue by flash chromatography (silica gel, hexane/ethylacetate 95/5) afforded 409 mg of pure, colorless title compound.

d] (E)-4-[2-(5-Ethoxymethyl-5-methyl-2,3,4,5-tetrahydrobenzo[b]thiepin-8-yl)-vinyl]benzoic acid 406 mg (0.99 mmol) of (E)-4-[2-(5-ethoxymethyl-5-methyl-2,3,4,5-tetrahydrobenzo[b]thiepin-8-yl)-vinyl]-benzoic acid methyl ester was dissolved in 4 ml of THF/ethanol=1/1 and treated with 1.32 ml of 3N NaOH(4 eq). The reaction flask was kept in the dark and stirring continued for 18 h at room temperature. The mixture was then poured onto crushed ice/diluted HCl, extracted twice with ethylacetate, the organic phase was washed with a small amount of water, dried over magnesium sulfate, filtrated and the solvent evaporated. Crystallization of the residue from hexane/ethylacetate (8/2) yielded 337 mg of the title compound as white crystals of m.p. 186–187° C.

NMR: (1 H, δ, TMS, DMSO) 1.10 (t, J=7, 3H), 1.43 (s, 3H), 1.65–2.15 (m,4H),, 2.79 (m, 2H), 3.46 (m, 2H), 3.61 (d, J=9, 1H), 3.88 (d, J=9, 1H), 7.33 (s, 2H), 7.42 (d, J=8, 1H), 7.50 (br d, J=S, 1H), 7.68 (br s, 1H), 7.71 (d, J=8.3, 2H), 7.93 (d, J=8.3, 2H), 12.92 (br s, COOH).

MS: (M)$^+$382, (M-CH$_2$OC$_2$H$_5$)$^+$323.

4.2. Preparation of (E)-4-[2-(5-methoxymethyl-5-propyl-2,3,4,5-tetrahydrobenzo[b]thiepin-8-yl)-vinyl]-benzoic acid

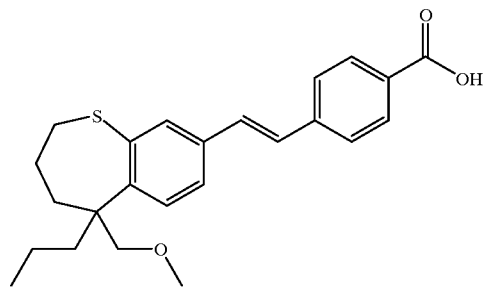

This compound was prepared in analogy to Example 4.1.; White crystals of m.p. 169–170° were obtained, but using in step c] 5-methoxymethyl-5-propyl-2,3,4,5-tetrahydrobenzo[b]thiepine-8-carbaldehyde instead of 5-ethoxymethyl-5-methyl-2,3,4,5-tetrahydrobenzo[b]thiepine-8-carbaldehyde. The former had been prepared in analogy to Example 2.1., a]–d], but starting the whole reaction sequence with 8-bromo-3,4-dihydro-2 H-benzo[b]thiepin-5-one instead of the oxa-analogue. White crystals of m.p. 169–170° were obtained.

CI-MS: (M-H)$^+$395.

EXAMPLE 5

5.1. Preparation of 4-(4-methoxymethyl-4-methyl-chroman-6-ylethynyl)-benzoic acid

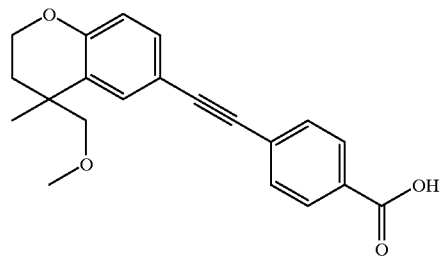

a] 4-Methyl-chroman-4-carbaldehyde 5.28 g (32.55 mmol) of chroman-4-carbaldehyde was dissolved in 100 ml of abs. THF/abs. tert.-butanol (5/1). At −10° C., 7.31 g (2 eq.) of potassium tert.-butylate was added, followed after 0.25 h by 4.05 ml (2.0 eq.) of methyliodide. Stirring was continued at room temperature over night. The reaction mixture was then poured onto crushed ice and extracted twice with diethylether, the organic phase was washed with brine, dried over magnesium sulfate, filtrated and the solvent was removed. Flash chromatography (SiO$_2$, hexane/ethylacetate 9/1) yielded 4.29 g of the title compound as colorless oil (96.5% pure according to GC).

MS: (M)$^+$176, (M-HCO)$^+$147.

b] (4-Methyl-chroman-4-yl)-methanol 4.29 g (24.3 mmol) of 4-methyl-chroman-4-carbaldehyde was dissolved in 160 ml of abs. ethanol and cooled to 0° C. 0.921 g (1 mol-eq.) of NaBH$_4$ was added in several portions and the reaction allowed to proceed for 16 h at room temperature. Pouring onto crushed ice, twofold extraction with diethylether, washing the organic phase with water, and drying it over magnesium sulfate left, after filtration and evaporation of the solvent, 4,41 g of the title compound as pale yellow oil, sufficiently pure for the next step (GC:>97%).

c] 4-Methoxymethyl-4-methyl-chroman 2.00 g (11.2 mmol) of (4-methyl-chroman-4-yl)-methanol was dissolved in 60 ml of abs. DMF and treated at 0° with 1.08 g of NaH (ca. 50% in mineral oil, ca. 2 eq.). Deprotonation was allowed to proceed at 0° C. for 0.75 h. When evolution of hydrogen had ceased, the mixture was treated with 1.05 ml of methyliodide (1.5 eq.) and then kept for 0.2 h at 0° C. and for 0.5 h at room temperature. Careful hydrolysis with cold water, twofold extraction with diethylether, washing the organic phase with water, drying it over magnesium sulfate, left, after filtration and evaporation of the solvent, a crude product, which was purified by flash chromatography over SiO$_2$ (hexane/ethylacetate 9/1) to give 2.01 g of the title compound as colorless oil (97% pure according to GC).

MS: (M)$^+$192, (M-CH$_2$OCH$_3$)$^+$147.

d] 6-Bromo-4-methoxymethyl-4-methyl-chroman 2.00 g (10.4 mmol) of 4-methoxymethyl-4-methyl-chroman was dissolved in 25 ml of abs. CH$_2$Cl$_2$ and treated with a catalytic amount of Fe-powder and $Na_2CO_3$. After cooling to 0° C., 1.21 m of bromine (1.1 eq.) was added and the mixture kept for 0.6 h at this temperature. Pouring onto crushed ice, extraction with diethylether, washing the organic phase with water, drying it over magnesium sulfate, filtration and evaporation of the solvents, and ensuing flash chromatography over $SiO_2$ (hexane/ethylacetate 95/5) yielded 1.676 g of pure title compound as colorless oil (GC>95%).

MS: $(M)^+$270,272, $(M-CH_2OCH_3)^+$225,227.

e] (4-Methoxymethyl-4-methyl-chroman-6-ylethynyl)-trimethylsilane

To 1.67 g (6.16 mmol) of 6-bromo-4-methoxymethyl-4-methyl-chroman, dissolved in 11.5 ml of piperidine, was added successively 19 mg (0.02 eq.) of CuI, 27.5 mg (0.02 eq.) of triphenylphosphine ($Ph_3P$), and 93 mg (0.01 eq.) of $(Ph_3P)_4Pd$. After heating to 80° C., a solution of 4.27 ml (5 eq.) of trimethylsilyl-acetylene in 19 ml of piperidine was added within 2.5 h via dropping funnel. After cooling, the reaction mixture was poured onto crushed ice, extracted with diethylether, the organic phase was washed with water, dried over magnesium sulfate, filtrated and the solvent was evaporated. Flash chromatography ($SiO_2$, hexane/ethylacetate 95/5) of the residue afforded 1.44 g of the title compound as colorless oil, sufficiently pure for the next step.

f] 6-Ethynyl-4-methoxymethyl-4-methyl-chroman

A catalytic amount of sodium was dissolved in 22 ml of abs. methanol. To the resultant solution of sodium methylate was then added in one portion the above prepared (4-methoxymethyl-4-methyl-chroman-6-ylethynyl)-trimethylsilane (1.44g, 4.99 mmol), dissolved in a small amount of methanol, at 0° C. and then kept for 1 h at room temperature. The reaction mixture was poured onto crushed ice, extracted twice with diethylether, the organic phase was dried over magnesium sulfate, filtrated and the solvents were removed. Flash chromatography ($SiO_2$, hexane/ethylacetate 96/4) yielded 0.704 g of the title compound as a pale yellow oil, >94% pure according to GC.

MS: $(M)^+$216, $(M-CH_2OCH_3)^+$171.

g] 4-(4-Methoxymethyl-4-methyl-chroman-6-ylethynyl)-benzoic acid methyl ester

In 11 ml of abs. DMF was successively dissolved 1.061 g (1.25 eq.) of methyl 4-iodo-benzoate, 114 mg (0.05 eq.) of bis (triphenylphosphine)palladium(II) chloride, 74.1 mg (0.12 eq.) of CuI, and 1.13 ml (2.5 eq.) of triethylamine. 701 mg (3.24 mmol) of the above prepared 6-ethynyl-4-methoxymethyl-4-methyl-chroman, dissolved in 2.7 ml of abs. DMF, was added within 1 h via dropping funnel. After 0.25 h, the reaction was quenched by pouring the reaction mixture onto crushed ice/ HCl. Extraction with diethylether, washing the organic phase twice with water, drying it over magnesium sulfate, filtration and evaporation of the solvent yielded after flash chromatography ($SiO_2$, hexane/ ethylacetate 92/8) 630 mg of the title compound as yellowish oil.

h] 4-(4-Methoxymethyl-4-methyl-chroman-6-ylethynyl)-benzoic acid 625 mg (1.78 mmol) of 4-(4-methoxymethyl-4-methyl-chroman-6-ylethynyl)-benzoic acid methyl ester was dissolved in 9 ml of THF/ethanol (1/1) and treated with 2.34 ml of 3N NaOH (4 eq.). The reaction flask was kept in the dark and stirring continued for 18 h at room temperature. The mixture was then poured onto crushed ice/ HCl, extracted twice with diethylether, the organic phase was washed with water, dried over magnesium sulfate, filtrated and the solvent was evaporated. Crystallization from ethylacetate yielded 545 mg of the title product as white crystals of m.p. 202–203° C.

NMR: (1H, δ, TMS, DMSO) 1.27 (s, 3H), 1.66 (dxdxd, 1H), 2.02 (dxdxd, 1H), 3.26 (s,3H), 3.39 (d, J=9, 1H), 3.50 (d, J=9, 1H), 4.19 (m, 2H), 6.80 (d, J=8.4, 1H), 7.30 (dxd, J=8.4, J=2, 1H), 7.57 (d, J=2, 1H), 7.63 (d, J=8.3, 2H), 7.95 (d, J=8.3, 2H), 13.14 (br s, COOH).

MS: $(M)^+$336, $(M-CH_2OCH_3)^+$291.

EXAMPLE 6

6.1. Preparation of (E)-4-(4-hydroxymethyl-4-methyl-chroman-6-ylethynyl)-benzoic acid a] Acetic acid 4-methyl-chroman-4-ylmethyl ester 1.00 g (5.61 mmol) of (4-methyl-chroman-4-yl)-methanol was dissolved in 6 ml of abs. $CH_2Cl_2$, treated at 0° C. with 1.17 ml (1.5 eq. ) of triethylamine and 0.518 ml (1.3 eq.) of acetylchloride and then kept for 0.5 h at room temperature. The reaction mixture was poured onto crushed ice and extracted twice with diethylether; the organic phase was washed with water, dried over sodium sulfate, filtrated and the solvents were removed. Flash chromatography (SiO2, hexane/ethylacetate 9/1) gave 1.082 g of pure title compound as colorless oil.

MS: $(M)^+$220, $(M-CH_2OAc)^+$147.

b] Acetic acid 6-bromo-4-methyl-chroman-4-ylmethyl ester

Was prepared in analogy to Example 5d], by bromination of the above prepared acetic acid 4-methyl-chroman-4-ylmethyl ester.

MS: $(M)^+$298,300 $(M-CH_2OAc)^+$225,227.

NMR: (1 H, δ, TMS, DMSO) 1.29 (s, 3H), 1.69 (dxdxd, 1H), 1.99 (dxdxd, 1H), 4.08–4.2 (m, 4H),, 6.73 (d, J=8.7, 1H), 7.25 (dxd, J=8.7, J=2.4, 1H) 7.53 (d, J=2.4, 1H).

c] Acetic acid 4-methyl-6-trimethylsilanylethynyl-chroman-4-ylmethyl ester

Was prepared in analogy to Example 5e] from acetic acid 6-bromo-4-methyl-chroman-4-ylmethyl ester.

MS: $(M)^+$316 $(M-CH_2OAc)^+$243.

d] Acetic acid 6-ethynyl-4-methyl-chroman-4-ylmethyl ester

Was prepared in analogy to Example 5f] from acetic acid 4-methyl-6-trimethylsilanyl ethynyl-chroman-4-ylmethyl ester.

MS: $(M)^+$244 $(M-CH_2OAc)^+$171.

e] 4-(4-Acetoxymethyl-4-methyl-chroman-6-ylethynyl)-benzoic acid methyl ester

Was prepared in analogy to Example 5g] from acetic acid 6-ethynyl-4-methyl-chroman-4-ylmethyl ester.

MS: $(M)^+$378, $(M-CH_3O)^+$347, $(M-CH_2OAc)^+$305.

f] 4-(4-Hydroxymethyl-4-methyl-chroman-6-ylethynyl)-benzoic acid 498 mg (1.32 mmol) of 4-(4-acetoxymethyl-4-methyl-chroman-6-ylethynyl)-benzoic acid methyl ester was dissolved in 7 ml of THF/ethanol (1/1) and treated with 1.75 ml of 3N NaOH (4 eq.). The reaction flask was kept in the dark and stirring continued for 4 h at room temperature. The mixture was then poured onto crushed ice/ HCl, extracted twice with diethylether, the organic phase was washed with brine, dried over magnesium sulfate, filtrated and the solvent evaporated. Crystallization from ethylacetate at −30° C. yielded 334 mg of the title compound as off-white crystals of m.p. 234–235° C.

MS: $(M)^+$322, $(M-CH_2OH)^+$291.

IR($cm^{-1}$): 2924, 2854, 1678, 1602, 1564, 1490, 1429, 1317, 1377, 1294, 1228, 1173, 1018, 828, 771.

NMR: (1 H, δ, TMS, DMSO) 1.24 (s, 3H), 1.62 (dxdxd, 1H), 2.02 (dxdxd, 1H), 3.46 (dxd, 1H), 3.55 (dxd, 1H), 4.20 (m, 2H), 4.91 (br t, OH), 6.79 (d, J=8.4, 1H), 7.27 (dxd, J=8.4, J=2, 1H) 7.54 (d, J=2, 1H), 7.62 (d, J=8.3, 2H), 7.95 (d, J=8.3, 2H), 13.15 (br s, COOH).

EXAMPLE 7

Effects of RAR Selective Retinoids on Repair of Alveoli in Elastase-induced Emphysema RAR selective agonists were evaluated for its effects on alveolar repair in the rat model of elastase-induced emphysema in rats (Massaro et al. Nature (Medicine, 1997, 3, 675)). Animals were divided into treatment groups of approximately eight. Lung inflammation and alveolar damage was induced in male Sprague Dawley rats by a single instillation of pancreatic elastase(porcine derived, Calbiochem) 2 U/gram body mass. Three weeks post injury all-trans retinoic acid or RAR agonist was dissolved in dimethylsulfoxide (20 mg/ml) and stored at −20 C. Fresh working stocks were prepared fresh daily by dilution in PBS to a final concentration of 2 mg/ml. Animals treated with all-trans retinoic acid (0.5 mg/Kg ip) were dosed once daily by intraperitoneal injection, starting 21 days post injury. Control groups were challenged with elastase and 21 days later treated with Vehicle (DMSO/PBS) for 14 days. Animals were sacrificed 24 hours after the last dose of by exsanguination under deep anesthesia.

The lungs were inflated with 10% neutral buffered formalin by intratracheal instillation at a constant rate (1 ml/gram body mass/min). The lung was excised and immersed in fixative for 24 hours prior to processing. Standard methods were used to prepare 5 um paraffin sections. Sections were stained with Hematoxylin and Eosin (H%E). Computerized Morphometric analysis was performed to determine the average alveolar size and alveolar number (Table 1).

TABLE 1

| Dose [mg/kg] |      | % repair area | compound |
| --- | --- | --- | --- |
| 0.5 | i.p. | 58 | A |
| 0.1 | p.o. | 45.2 | A |
| 0.3 | p.o. | 51.3 | A | i.p. intraperitoneal
p.o. per os

The foregoing invention has been described in some detail by way of illustration and example, for the purposes of clarity and understanding. It will be obvious to one of ordinary skill in the art that changes and modifications may be practiced within the scope of the appended claims. Therefore, it is to be understood that the above description is intended to be illustrative and not restrictive. The scope of the invention should, therefore, be determined with reference to the following appended claims, along with the full scope of equivalents to which such claims are entitled.

The patents, patent applications and publications cited in this application are hereby incorporated by reference in their entirety for all purposes to the same extent as if each individual patent, patent application or publication were so individually denoted. The contents of European Patent Application No. 99116603.4, filed Aug. 25, 1999, are incorporated herein by reference.

What is claimed is:

1. A retinoid in racemic or (R) or (S) stereoconfiguration, wherein the retinoid is a compound of formula I

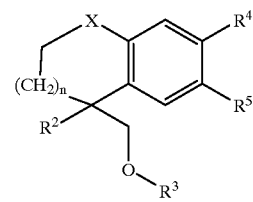

wherein
one of $R^4$ and $R^5$ is hydrogen and the other is $R^1$ is hydrogen or lower alkyl;
$R^2$ is lower alkyl;
$R^3$ is hydrogen or lower alkyl;
X is oxygen or sulfur;
n is 1 or 2; and
wherein the dotted bond is optional;
or when $R^1$ is hydrogen, a pharmaceutically active salt of the compound.

2. The retinoid according to claim 1, wherein X is oxygen and n is 2.

3. The retinoid according to claim 1, wherein X is sulfur and n is 2.

4. The retinoid according to claim 1, wherein X is oxygen and n is 1.

5. The retinoid according to claim 1, wherein the retinoid is the pharmaceutically active salt of the compound formed from a pharmaceutically acceptable base.

6. The retinoid according to claim 5, wherein the pharmaceutically active salt is an alkali salt, ammonium salt, or substituted ammonium salt.

7. The retinoid according to claim 1 in racemic form.

8. The retinoid according to claim 1 in the (R) stereoconfiguration, substantially free of the corresponding (S) isomer.

9. The retinoid according to claim 1 in the (S) stereoconfiguration, substantially free of the corresponding (R) isomer.

10. A retinoid according to claim 1, wherein the retinoid is a compound of formula

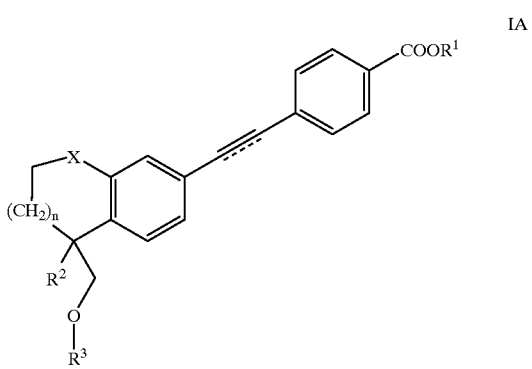

wherein X, $R^1$, $R^2$, $R^3$ and n are as defined in claim 1; or when $R^1$ is hydrogen, a pharmaceutically active salt of the compound.

11. The retinoid according to claim 10, wherein X is oxygen and n is 2.

12. The retinoid according to claim 11, wherein the compound is 4-(5-methoxymethyl-5-methyl-2,3,4,5-tetrahydro-1-benzo[b]oxepin-8-yl-ethynyl)-benzoic acid.

13. The retinoid according to claim 11, wherein the compound is 4-(5-ethoxymethyl-5-methyl-2,3,4,5-tetrahydrobenzo[b]oxepin-8-ylethynyl)-benzoic acid.

14. The retinoid according to claim 11, wherein the compound is 4-(5-methyl-5-propoxymethyl-2,3,4,5-tetrahydrobenzo[b]oxepin-8-ylethynyl)-benzoic acid.

15. The retinoid according to claim 11, wherein the compound is (E)-4-[2-(5-methoxymethyl-5-propyl-2,3,4,5-tetrahydrobenzo[b]oxepin-8-yl)-vinyl]-benzoic acid.

16. The retinoid according to claim 11, wherein the compound is (E)-4-[2-(5-methoxymethyl-5-methyl-2,3,4,5-tetrahydrobenzo[b]oxepin-8-yl)-vinyl]-benzoic acid.

17. The retinoid according to claim 11, wherein the compound is (E)-4-[2-(5-methyl-5-propoxymethyl-2,3,4,5-tetrahydrobenzo[b]oxepin-8-yl)-vinyl]-benzoic acid.

18. The retinoid according to claim 10, wherein X is sulfur and n is 2.

19. The retinoid according to claim 18, wherein the compound is 4-(5-methoxymethyl-5-methyl-2,3,4,5-tetrahydrobenzo[b]thiepin-8-ylethynyl)-benzoic acid.

20. The retinoid according to claim 18, wherein the compound is 4-5-ethoxymethyl-5-methyl-2,3,4,5-tetrahydrobenzo[b]thiepin-8-ylethynyl)-benzoic acid.

21. The retinoid according to claim 18, wherein the compound is (E)-4-[2-(5-ethoxymethyl-5-methyl-2,3,4,5-tetrahydrobenzo[b]thiepin-8-yl)-vinyl]-benzoic acid.

22. The retinoid according to claim 18, wherein the compound is (E)-4-[2-(5-methoxymethyl-5-propyl-2,3,4,5-tetrahydrobenzo[b]thiepin-8-yl)-vinyl]-benzoic acid.

23. The retinoid according to claim 10, wherein the retinoid is the pharmaceutically active salt of the compound formed from a pharmaceutically acceptable base.

24. The retinoid according to claim 23, wherein the pharmaceutically active salt is an alkali salt, ammonium salt, or substituted ammonium salt.

25. A retinoid according to claim 1, wherein the retinoid is a compound of formula

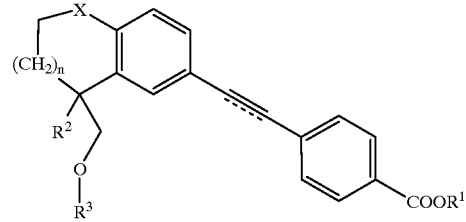

IB wherein X, $R^1$, $R^2$, $R^3$ and n are as defined in claim 1; or
when $R^1$ is hydrogen, a pharmaceutically active salt of the compound.

26. The retinoid according to claim 25, wherein X is oxygen and n is 1.

27. The retinoid according to claim 26, wherein the compound is 4-(4-methoxymethyl-4-methyl-chroman-6-ylethynyl)-benzoic acid.

28. The retinoid according to claim 26, wherein the compound is (E)-4-[2-(4-methoxymethyl-4-methyl-chroman-6-yl)-vinyl]-benzoic acid.

29. The retinoid according to claim 25, wherein the retinoid is the pharmaceutically active salt of the compound formed from a pharmaceutically acceptable base.

30. The retinoid according to claim 29, wherein the pharmaceutically active salt is an alkali salt, ammonium salt, or substituted ammonium salt.

* * * * *